United States Patent
Adoram et al.

(10) Patent No.: US 7,068,867 B2
(45) Date of Patent: Jun. 27, 2006

(54) ULTRASONIC POSITION INDICATOR

(75) Inventors: Avner Adoram, Ramat Hasharon (IL); Benny Pesach, Rosh-Ha'ayin (IL); Ron Nagar, Tel-Aviv (IL); Shai Ashkenazi, Rehovot (IL); Michal Balberg, Jerusalem (IL)

(73) Assignee: Glucon Medical Ltd, Petach-Tikva (IL)

( * ) Notice: Subject to any disclaimer, the term of this patent is extended or adjusted under 35 U.S.C. 154(b) by 0 days.

(21) Appl. No.: 10/335,703

(22) Filed: Jan. 2, 2003

(65) Prior Publication Data
US 2004/0131299 A1     Jul. 8, 2004

(51) Int. Cl.
*G02B 6/00*     (2006.01)

(52) U.S. Cl. .......................................... 385/12; 385/7
(58) Field of Classification Search .................. 385/12, 385/7; 606/1–3, 14–16
See application file for complete search history.

(56) References Cited

U.S. PATENT DOCUMENTS

| | | | |
|---|---|---|---|
| 5,350,377 A * | 9/1994 | Winston et al. ................ | 606/15 |
| 6,238,426 B1 * | 5/2001 | Chen ............................ | 607/88 |
| 6,514,249 B1 * | 2/2003 | Maguire et al. ............... | 606/41 |
| 6,863,653 B1 * | 3/2005 | Zanelli et al. ............... | 600/437 |
| 2001/0055435 A1 * | 12/2001 | Biagi et al. ..................... | 385/7 |
| 2002/0058890 A1 * | 5/2002 | Visuri et al. ................... | 601/4 |
| 2004/0067000 A1 * | 4/2004 | Bates et al. .................... | 385/7 |

* cited by examiner

*Primary Examiner*—Juliana Kang
(74) *Attorney, Agent, or Firm*—Mintz, Levin, Cohn, Ferris, Glovsky and Popeo, P.C.; Shane H. Hunter

(57) ABSTRACT

A system for monitoring a position of an instrument in a subject includes a light transmission medium configured to transmit light pulses to a desired region to produce an acoustic signal, at least one ultrasound sensor configured to receive the acoustic signal and to produce a transduced signal from the acoustic signal, and a processing unit connected to the at least one ultrasound sensor and configured to locate a source of the acoustic signal using the transduced signal.

25 Claims, 12 Drawing Sheets

ULTRASONIC POSITION INDICATOR

FIELD OF THE INVENTION

The invention relates to imaging internal regions of a subject and more particularly to monitoring positions of instruments inside the subject using ultrasonic imaging.

BACKGROUND OF THE INVENTION

For many surgical procedures the use of minimally-invasive surgical tools/instruments is widely accepted. Such surgical instruments include needles, endoscopes (a bundle of optical fibers, or a small camera encapsulated by a catheter), and catheters. These instruments may be used for procedures such as biopsies, endoscopic imaging, and cardiac catheterization surgeries. These procedures are performed, e.g., to diagnose tissues or organs suspected of being cancerous or otherwise in need of treatment, and for treating cardiac disease or malfunction.

Several techniques exist for monitoring the position of an instrument inside a human, including X-Ray fluoroscopy. Conventional X-Ray fluoroscopy is designed to reduce/minimize X-ray dosage, but long procedures can produce significant doses in the patient. Further, long-term exposure of personnel conducting X-Ray fluoroscopy procedures is a concern. Also, metal instruments produce a very strong signal in response to X-rays, saturating detectors and thus producing a "halo" around the instrument's image such that a tip of the instrument may be obscured.

Other techniques for monitoring instrument position include using ultrasound or electromagnetic radiation. Ultrasound is common because when operated at low power its energy is not hazardous and because soft tissues in the body that contain water are ideal for transmitting and reflecting sound waves. An ultrasound imager transmits sound waves to a specific area in the body and detects reflected signals. The imager forms a gray-scale image where the position of each feature is calculated from the delay in the reflected sound wave, and different intensities of reflected signals appear as different levels of gray in the image. A high impedance mismatch between the instrument and the surrounding tissues results in strong scattering of the sound waves. Another challenge with locating the tip of an instrument using ultrasound results from the two-dimensional scanning nature of the ultrasound imaging procedure. At any given time, the operator can view the cross section of the instrument in the plane "cut out" by the array. Consequently, only when the instrument is coplanar with the scanning motion can one identify its shape and locate its tip easily; at any other angle only the part of the instrument that is coplanar with the imaged plane can be identified. To improve the acoustic signature of instruments, passive and active acoustic reflectors or transducers may be attached to instruments as discussed in U.S. Pat. No. 4,431,006 and U.S. Pat. No. 4,697,595, respectively.

Still other techniques exist for monitoring instrument location inside of a subject. Ultrasound transducers can be integrated with instruments such as a catheter. A position sensor may be attached to a needle and convey position information to an imager. A low-power RF emitter may be attached to the tip of an instrument and RF sensors outside of the body may be used to detect the position of the emitter. Non-concentric coils may be attached to an instrument to produce signals in response to externally-applied magnetic fields to allow determination of position and orientation of an instrument attached to the coils. Further, ultrasound pulses can be produced outside of a subject, conveyed to the inside of the subject using acoustical fibers, and reflected signals collected and transmitted with these same fibers.

SUMMARY OF THE INVENTION

In general, in an aspect, the invention provides a system for monitoring a position of an instrument in a subject. The system includes a light transmission medium configured to transmit light pulses to a desired region to produce an acoustic signal, at least one ultrasound sensor configured to receive the acoustic signal and to produce a transduced signal from the acoustic signal, and a processing unit connected to the at least one ultrasound sensor and configured to locate a source of the acoustic signal using the transduced signal.

Implementations of the invention may include one or more of the following features. The system further includes a photoacoustic transducer including a photoacoustic material disposed in the desired region to absorb light transmitted by the light transmission medium to produce the acoustic signal. The light transmission medium is an optical fiber and the photoacoustic material is disposed at an end of the optical fiber. The photoacoustic material is a first photoacoustic material configured to produce a first frequency of sound from absorbed light, the system further comprising a second photoacoustic material configured to produce a second frequency of sound from absorbed light and coupled to the fiber distally from the first material, the first photoacoustic material being disposed and configured to absorb a first portion of light transmitted by the light transmission medium and to pass a second portion of the light transmitted by the light transmission medium. The optical fiber is coupled to the instrument. The end of the optical fiber, on which the photoacoustic material is disposed, is disposed a known distance from an end of the instrument. The light transmission medium comprises a plurality of optical fibers and the system further comprises position indicators coupled to the plurality of fibers. The position indicators comprise photoacoustic transducers including different photoacoustic materials configured to produce different frequencies of ultrasound signals, and wherein the processor is configured to distinguish between the photoacoustic transducers in accordance with the respective frequencies associated with the photoacoustic materials. The system further includes an optical driver coupled to the processor, wherein the processor is configured to cause the optical driver to provide optical signals to the plurality of optical fibers at different times, and wherein the processor is configured to distinguish between the position indicators in accordance with respective excitation times of the position indicators. The system further includes the instrument, wherein the position indicators are coupled to the instrument and have ultrasound-emitting portions that are disposed at least one of at known locations relative to the instrument and at known locations relative to each other. The system further includes a sensor disposed among the plurality of position indicators and coupled to the processor, the processor being further configured to determine distances from the sensor to the position indicators in response to information provided to the processor by the sensor. The system further includes the instrument, the instrument being further configured to selectively contain the plurality of position indicators and deploy ultrasound-emitting portions of the position indicators outside of the instrument. The instrument comprises a retractable sleeve for selectively containing and deploying the position indicators.

In general, in another aspect, the invention provides a system for monitoring a position of an instrument in a subject, the instrument being configured to be inserted into the subject. The system includes an array of ultrasound transducers configured to translate between ultrasound signals and electrical signals, an optical driver configured to provide optical excitation signals, a position indicator including an optical fiber, coupled to the optical driver and attached to the instrument, and a photoacoustic material disposed to absorb light transmitted by the optical fiber, a display configured to provide images in response to control signals, and a processor connected to the transducers, the optical driver, and the display, and configured to: actuate the array to emit ultrasound signals into the subject, receive first electrical signals from the array indicative of reflections of the emitted ultrasound signals, process the first electrical signals into first control signals indicative of a first image of the subject and to convey the first control signals to the display, actuate the driver to provide an excitation signal to the optical fiber, receive a second electrical signal from the array indicative of an ultrasound signal produced by the photoacoustic material, determine a position of the instrument from the second electrical signal, and process the second electrical signal into a second control signal indicative of a second image of the instrument and to convey the second control signal to the display.

Implementations of the invention may include one or more of the following features. The processor is configured to control the display to provide the images from the first and second control signals such that the first and second images at least appear to be provided concurrently. The processor is configured to actuate the transmission from the array and to actuate the optical driver at different, alternating times.

In general, in another aspect, the invention provides a method of monitoring a position of a position indicator relative to a subject, the indicator being disposed in a region inside the subject. The method includes applying first ultrasound signals to a region of the subject, detecting reflected and scattered ultrasound signals from the region of the subject in response to the applied first ultrasound signals, producing a subject image of the region of the subject from the reflected signals, transmitting an excitation signal into the region of the subject to the position indicator to produce another ultrasound signal at a location associated with the position indicator, determining a position of the position indicator from second ultrasound signals related to the other ultrasound signal, producing a position-indicator image from the second ultrasound signals, and superimposing the subject image and the position-indicator image.

Implementations of the invention may include one or more of the following features. Transmitting the excitation signal comprises transmitting light through an optical fiber, the method further comprising photoacoustically transducing the light into the another ultrasound signal and emitting the another ultrasound signal from the position indicator. The method further includes transmitting light through another optical fiber into the region of the subject to another position indicator, emitting a further ultrasound signal from the another position indicator, distinguishing between third ultrasound signals, related to the further ultrasound signal, and the second ultrasound signals based on at least one of timing of receipt of the second and third signals and frequencies of the second and third signals, and producing another position-indicator image from the third ultrasound signals. The method further includes deploying the position indicators from an instrument inserted into a volume in the region of the subject, allowing the position indicators to extend to one of their respective full extensions and into contact with a surface bounding the volume in the region of the subject, moving the instrument within the volume, and producing position-indicator images with the instrument at different positions within the volume. The method further includes calculating a volume of the body cavity in which the position indicators are deployed from relative positions of the indicators. The body cavity is a chamber of the heart. The volume is calculated separately during diastolic and systolic cycles, the method further comprising calculating cardiac output from a difference in the volume of the chamber during each cardiac cycle. Photoacoustically transducing the light into the another ultrasound signal comprises absorbing the light by a photoacoustic material disposed at a tip of the position indicator.

Implementations of the invention may also include one or more of the following features. The other ultrasound signal is produced by absorbing the excitation signal by a portion of the subject in the region. The method further includes determining a tissue type by using different wavelengths for generation of acoustic signals. Transmitting the excitation signal into the region of the subject comprises transmitting multiple excitation signals to multiple position indicators to produce multiple other ultrasound signals at locations associated with the multiple position indicators, the method further including sensing signals related to the other ultrasound signals with a sensor disposed among the multiple position indicators, and determining distances of the position indicators from the sensor. The method further includes determining distances from tips of the position indicators to a sensor disposed among the position indicators. The method further includes forming an ultrasound image of internal structures of the subject using ultrasound pulses emitted by the position indicators, scattered by the structures, and received by the sensor.

In general, in another aspect, the invention provides an instrument for use with an ultrasound imager for monitoring positions associated with the instrument while the instrument is disposed in a subject. The instrument includes a body having a proximal end and a distal end, the body being configured to be inserted into the subject, a first optical fiber coupled to the body and having a distal end disposed adjacent to the distal end of the body, and a first photoacoustic material on the first optical fiber configured to transduce optical signals received from the first optical fiber into first ultrasound signals and to emit the first ultrasound signals into the subject.

Implementations of the invention may include one or more of the following features. The distal end of the first optical fiber is disposed a known distance from the distal end of the body. The instrument further includes a second optical fiber coupled to the body and having a distal end, and a second photoacoustic material on the second optical fiber, the second photoacoustic material configured to transduce optical signals received from the second optical fiber into second ultrasound signals and to emit the second ultrasound signals into the subject, the first and second photoacoustic materials being configured such that frequencies of the first and second ultrasound signals are different. The first and second optical fibers are fixedly coupled to the body along portions of their lengths and distal portions of their lengths releasably contained by the body. The body includes a sleeve for releasably containing the distal portions of the optical fibers, the sleeve being movable between a first position for containing the distal portions of the fibers and a second position for deploying the distal portions of the fibers. The instrument further includes an acoustic sensor, configured to transduce acoustic signals, coupled to the body. The body is configured to be inserted into a human.

In general, in another aspect, the invention provides a system for monitoring the position of an instrument in a subject, the instrument being configured to be inserted into the subject. The system includes a plurality of ultrasound transducers configured to translate between ultrasound signals and electrical signals, driver means coupled to the ultrasound transducers for providing first excitation signals to the ultrasound transducers and for providing second excitation signals, position indicator means coupled to the driver and to the instrument for producing ultrasound signals in response to the second excitation signals from the driver means, and processor means, coupled to the transducers and the driver means, for controlling the driver means to cause the transducers to transmit first ultrasound signals into the subject, for determining an image of the subject from reflected subject signals related to the first ultrasound signals, for controlling the driver means to cause the position indicator means to produce a second ultrasound signals, for determining an indicator image corresponding to the position indicator means from indicator signals related to the second ultrasound signal, and for controlling a display to show an association between the indicator image and the image of the subject.

Implementations of the invention may include one or more of the following features. The driver means includes an electrical driver coupled to the transducers and an optical driver coupled to the position indicator means. The position indicator means includes a photoacoustic material on an optical fiber. The position indicator means includes multiple optical fibers each having a photoacoustic material on a respective tip. Different optical fibers of the position indicator means have different photoacoustic material characteristics that produce different frequencies of ultrasound. The position indicator means comprises multiple ultrasound emitters, the system further comprising an acoustic sensor configured to receive and transduce ultrasound from the multiple ultrasound emitters, and to transmit the transduced information to the processing means that is further for determining distances from the acoustic sensor to the multiple ultrasound emitters.

In general, in another aspect, the invention provides a method of monitoring a position of a position indicator relative to a subject, the indicator being disposed in a region inside the subject. The method includes applying first ultrasound signals to the region of the subject, detecting first reflected ultrasound signals from the region of the subject in response to the applied first ultrasound signals, storing a first image obtained from the first reflected ultrasound signals, applying second ultrasound signals to the region of the subject at a first time, providing an excitation signal to the position indicator at a second time, after the first time, detecting second reflected ultrasound signals and the acoustic signal produced by the position indicator from the region of the subject, storing a second image obtained from the second reflected ultrasound signals and the acoustic signal produced by the position indicator, comparing the first and second images to produce a position-indicator image to isolate the acoustic signal produced by the position indicator, determining the position of the position indicator from the position-indicator image, and superimposing an image of the subject and the position-indicator image.

Implementations of the invention may include one or more of the following features. The image of the subject used for the superimposing is the first image, and wherein the comparing comprises subtracting one of the first and second images from the other of the first and second images. The image of the subject used for the superimposing is the first image, and wherein the comparing comprises high pass filtering of a difference between the first and second images.

In general, in another aspect, the invention provides a method of monitoring a position of a position indicator relative to a subject, the indicator being disposed in a region inside the subject. The method includes applying first ultrasound signals to a region of the subject, detecting first reflected ultrasound signals from the region of the subject in response to the applied first ultrasound signals, storing a first image obtained from the first reflected ultrasound signals, applying second ultrasound signals to the region of the subject, detecting the second ultrasound signal at the position indicator, providing an excitation signal to the position indicator to produce an acoustic signal substantially when the second ultrasound signal reaches the position indicator, detecting second reflected ultrasound signals and the acoustic signal produced by the position indicator from the region of the subject, storing a second image obtained from the second reflected ultrasound signals and the acoustic signal produced by the position indicator, comparing the first and second images to produce a position-indicator image to isolate the acoustic signal produced by the position indicator, determining the position of the position indicator from position-indicator image, and superimposing an image of the subject and the position-indicator image.

Implementations of the invention may include one or more of the following features. The image of the subject used for the superimposing is the first image, and wherein the comparing comprises subtracting one of the first and second images from the other of the first and second images. The image of the subject used for the superimposing is the first image, and wherein the comparing comprises high pass filtering of a difference between the first and second images.

Various aspects of the invention may provide one or more of the following advantages. A low-cost, disposable ultrasound source can be disposed on an instrument inserted into a body for emitting ultrasound that is detectable outside of the body, or at another location within the body. An ultrasound source can be provided on a surgical instrument and excited without using electric wires or external attachment to the instrument. Surgical instrument positioning can be determined without being affected by electromagnetic interference. Different tissue types may be identified using a surgical instrument positioning system. Different instruments may be concurrently disposed in a subject and have their respective positions identified independently. The orientation of an instrument relative to body features or fiducial markers can be identified easily. Images of position indicators can be superimposed on/with images of a subject. Volumes/geometries of cavities, vessels, etc. can be calculated more precisely than using techniques that do not superimpose indicator images and subject images. A subject and an instrument disposed in the subject can be imaged using the same imaging modality. These and other advantages of the invention, along with the invention itself, will be more fully understood after a review of the following figures, detailed description, and claims.

DETAILED DESCRIPTION OF PREFERRED EMBODIMENTS

Exemplary embodiments of the invention provide techniques for monitoring the position of a tool/instrument inside of a subject such as a human body. An optical fiber is connected to the instrument with a distal end of the fiber disposed near (and/or at a known distance from) a tip of the instrument. The distal end of the fiber is coated with a photoacoustic material and light is transmitted through the fiber from the proximal end to the distal end, absorbed by the coating, producing an ultrasound wave emanating from the photoacoustic material. The ultrasound waves from the fiber are detected by an ultrasound imager that is preferably disposed outside the subject. The imager produces an image of the fiber tip and overlays that with an image that the imager produces of the subject. Other embodiments are within the scope and spirit of the invention and the appended claims.

Figure 1:
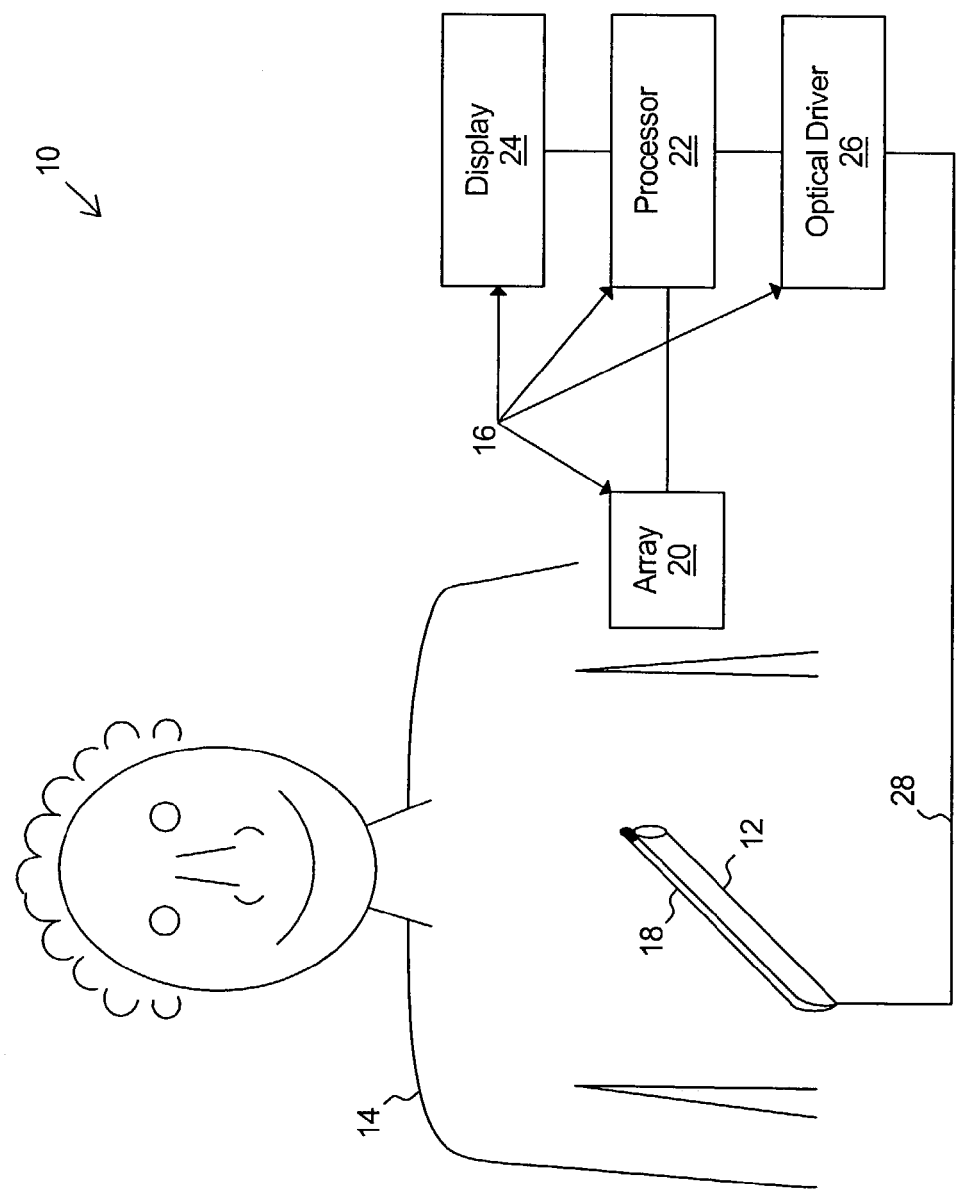
FIG. 1 is a simplified diagram of an ultrasound system for monitoring a position of a position indicator.

Referring to FIG. 1, a system 10 for monitoring the location of an instrument 12 in a subject 14 includes an ultrasound imager 16 and a position indicator 18. The subject 14 is shown as a human being, but the system and use of the system can be applied to other subjects such as other animals or even inanimate objects. The instrument 12 can be any of a variety of instruments for use in minimally-invasive surgical procedures such as a catheter, an endoscope, a needle, a guidewire, etc. For human subjects, the instrument 12 is preferably of surgical grade.

The ultrasound imager 16 is configured to produce images of the subject 14 and images of the position indicator 18. For imaging the subject 14, the imager 16 is configured in a conventional way with known apparatus. Thus, the imager 16 includes an array 20 of transducers, responsive to electric excitation signals from a driver (e.g., a voltage or current source under control of a processor 22), for transmitting ultrasound signals and/or receiving corresponding reflected ultrasound signals. The transducers can convert these reflected signals to electrical signals and transmit the electrical signals to the processor 22 of the imager. The processor 22 is configured (e.g., with appropriate software and electronics) to determine a subject image (e.g., intensities of pixels for a black-and-white image) and to transmit indicia of the image to a display 24 for displaying the image. For imaging the position indicator 18, the imager 16 includes an optical driver 26 coupled to the processor 22 and configured to supply optical excitation signals through an optical fiber 28 to the position indicator 18. The position indicator 18 is configured to produce ultrasound signals (as discussed below) in the vicinity of a distal end of the indicator 18 that can be detected by the array 20. The detected signals are converted to a position indicator image (as discussed below) in a manner similar to the production of the subject image (as described above). The processor 22 is configured to coordinate application of ultrasound signals through the array 20 and application of optical signals from the driver 26 to image both the subject 14 and the position indicator 18 at or near the same time and to superimpose images of each on the display 24. Displayed images of the position indicator 18 can be of a different color (or display modality, such as blinking or other types of display features) than of the subject 14 (ultrasound subject images are typically black-and-white images). Also, images of the subject 14 and of the indicator 18 may be alternated quickly such that effectively an observer sees what appears to be superimposed, concurrently-displayed images. Preferably, the indicator 18 is not excited during imaging of the subject, and the array 20 does not transmit during imaging of the indicator 18. In another embodiment, both imager and indicator can be operated simultaneously, with different modes of operation as discussed below.

Figure 2:
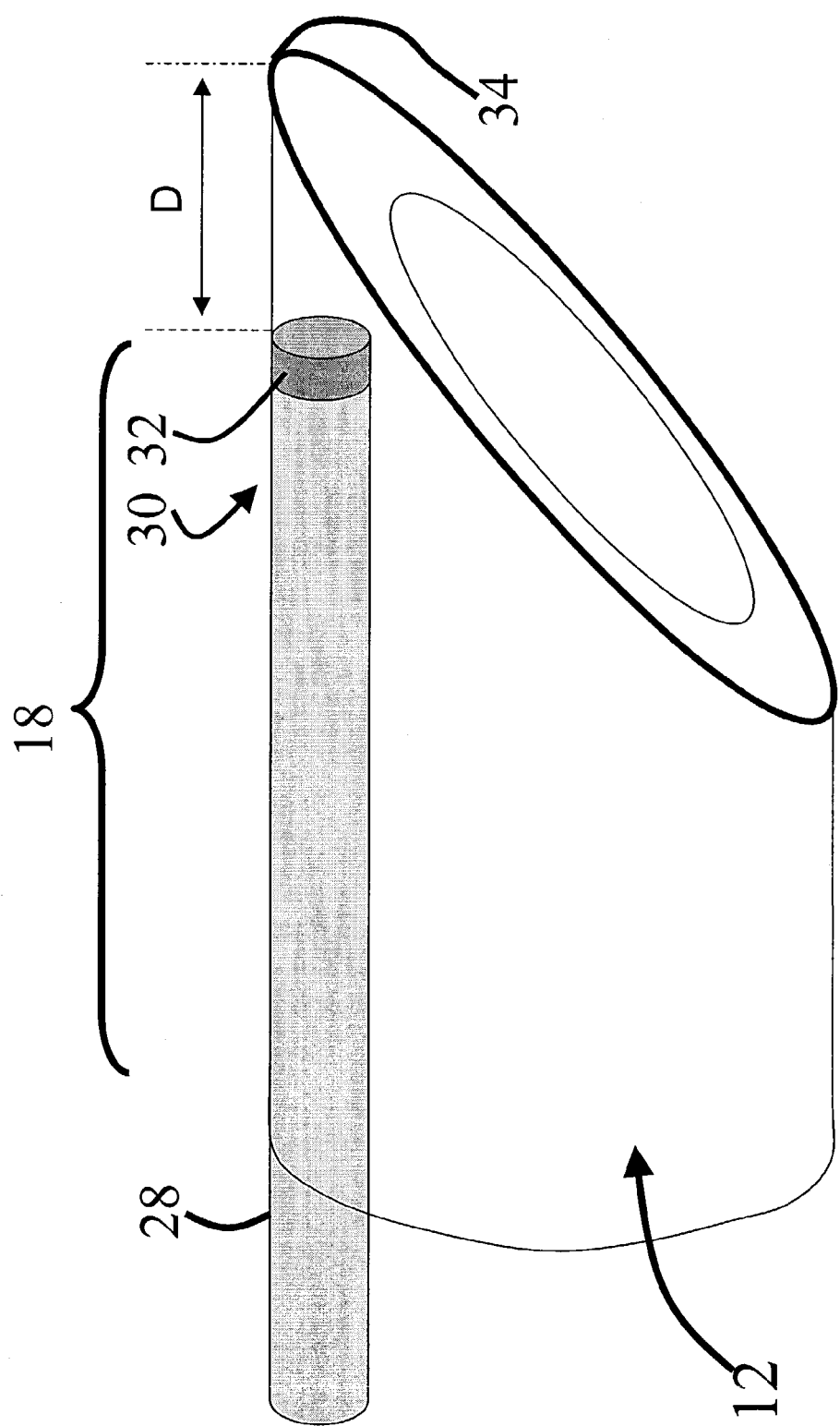
FIG. 2 is a simplified, see-through perspective view of a position indicator disposed in a needle.

Referring to FIG. 2, the position indicator 18 includes a distal end 30 of the optical fiber 28 and a photoacoustic transducer 32. Here, the photoacoustic transducer 32 is a photoacoustic coating, although other forms of transducers may be used. The indicator 18 is disposed inside the instrument 12 (here, a needle) with the transducer 32 located a known distance D from a tip 34 of the instrument 12. The coating 32 is configured to absorb optical signals transmitted through the fiber 28 to produce corresponding acoustic waves. Exemplary photoacoustic materials for the coating 32 include, but are not limited to, graphite, graphite/epoxy resin mixtures, silicon elastomers (e.g., polydimehtylsiloxaine) mixed with absorbing particles such as carbon black or graphite, and metals (e.g., aluminum). Preferably, the coating 32 has a higher optical absorption coefficient than water at the wavelength used for generation of a photoacoustic signal. Assuming a coating with an absorption coefficient of water, the coating 32 can produce an acoustic signal with a pressure amplitude of at least about $6 \cdot 10^3$ Pascal, with a signal-to-noise ratio (SNR) at the array 20 (FIG. 1) of approximately 122:1, in response to light pulses from a conventional laser or a diode laser (energy of a few microJoules). This will provide an acceptable acoustic signal at the array 20 if the array 20 has a detection limit of about 1 Pascal or better, assuming the instrument is embedded inside a body tissue at a depth of 10–15 cm.

Light pulses absorbed by the coating 32 produce sound waves via the photoacoustic effect. Thus, the characteristics of the coating 32 material, such as its optical absorption coefficient, its thermal expansion coefficient and other acoustic characteristics (such as sound velocity or bulk modulus) and its thickness and characteristics of the optical pulses absorbed, affect the frequency and amplitude (i.e., the coating's acoustic signature) of the acoustic waves produced by the coating 32. The choice of acoustic parameters depends on the application of the instrument, for example if deep penetration into the body of a subject is required, a low frequency signal (<1 MHz), that is less attenuated by the tissue should be used. In cases where high resolution is required but the penetration depth is low (as described below for scanning of blood vessels), higher frequencies (>10 MHz) could be generated. The acoustic signature of the coating 32 can be determined and calibrated by the imager 16 (FIG. 1), such that multiple coatings 32 can be distinguished by the imager 16, as discussed below with respect to FIG. 7.

Figure 3:
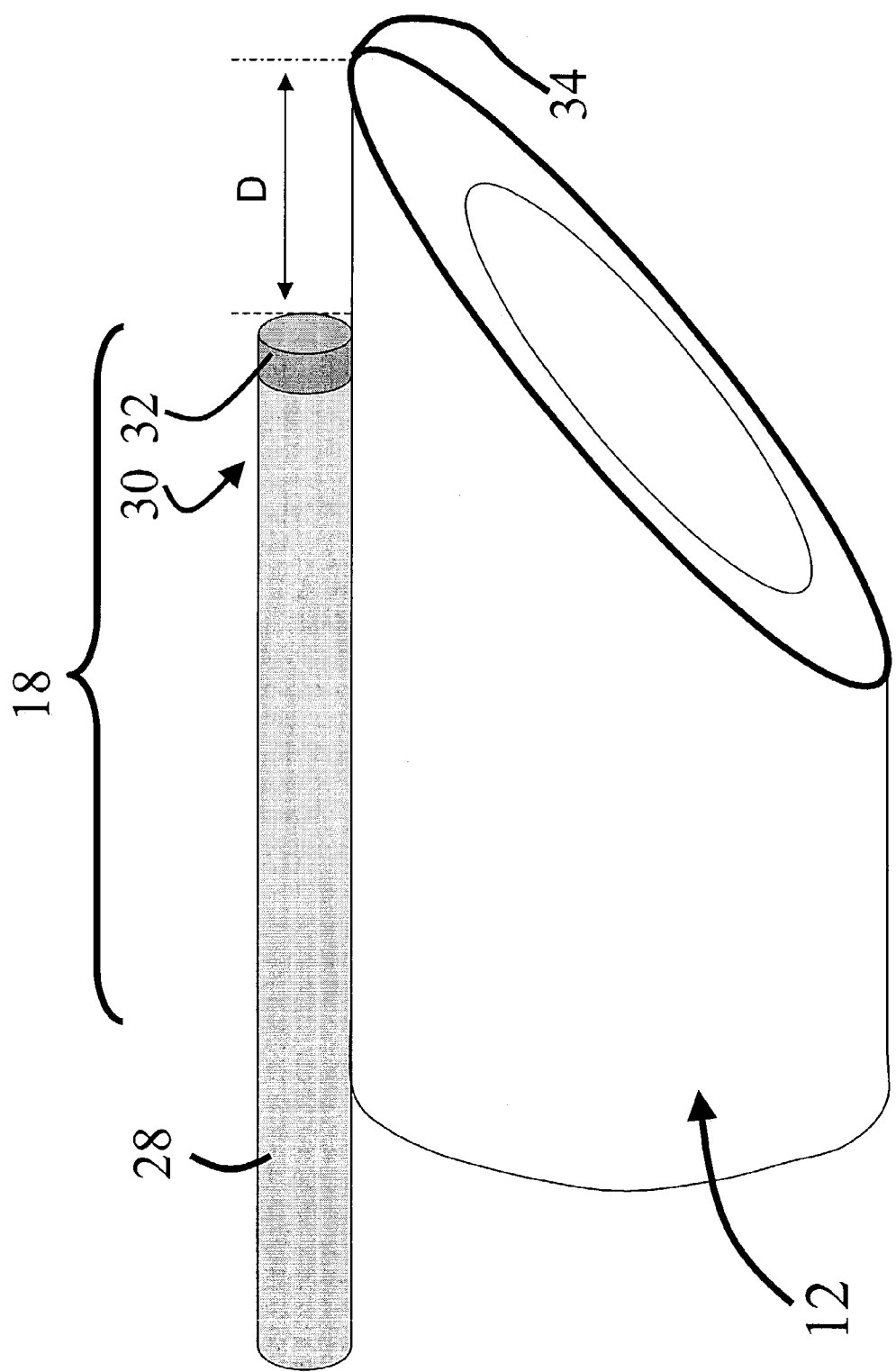
FIG. 3 is a simplified, see-through perspective view of a position indicator disposed externally to a needle.

Different configurations of the instrument 12 and the position indicator 18, and different instruments 12, may be used. For example, referring to FIG. 3, the instrument 12 is a needle as in FIG. 2, but the position indicator 18 is disposed externally to the instrument 12. Also, referring to FIG. 4, the position indicator 18 is disposed internally to the instrument 12 (here, inside the lumen), with the instrument 12 being a hollow catheter. The fiber 28 is preferably disposed in a track or groove in the wall of the needle. As shown, the coating 32 may be disposed at or very near a distal end 36 of the catheter.

Figure 4:
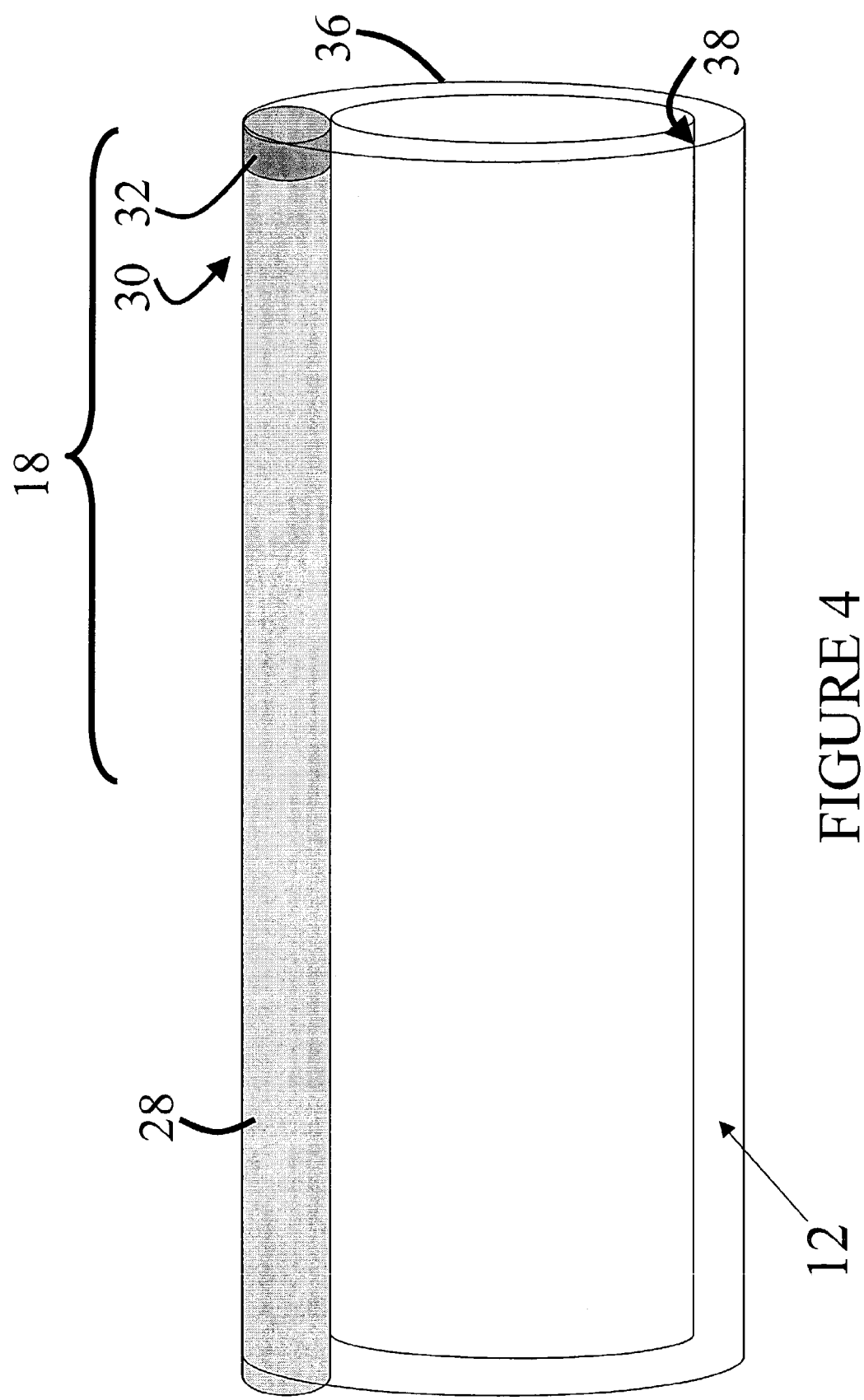
FIG. 4 is a simplified, see-through perspective view of a position indicator disposed in a catheter.

Referring again to FIG. 1, the fiber 28 can be attached to any of various acceptable instruments 12. For example, for a catheter as shown in FIG. 4, a cylindrical track or groove can be made in a wall 38 of the instrument 12, preferably with a diameter substantially equal to that of the fiber 28 (e.g., a few hundred microns). The track can be internal to the instrument 12 or can be external to the instrument 12 (e.g., a partially-cylindrical track). To inhibit sliding of the fiber 28 in the track, glue may be applied to the instrument 12 and/or the fiber 28 at one or more places along the track. For a needle, referring also to FIG. 2, a track can be made in the guiding catheter of the needle. In the needle itself, the track should be external to the lumen to help prevent blocking of the lumen, e.g., for biopsies. In some embodiments, the tip of the position indicator 18 should not be attached to the instrument 12 so that the coating coincides with the tip 34 of the needle to help prevent interfering of the indicator 18 with the tip 34. In embodiments such as a catheter or an endoscope, however, the tip of the position indicator 18 can preferably coincide with the tip of the instrument 12. When the instrument 12 is an endoscope, for example, one (and possibly more) of the optical fibers composing the endoscope fiber bundle may be coated, without significantly sacrificing the performance of the endoscope for internal viewing.

Figure 5:
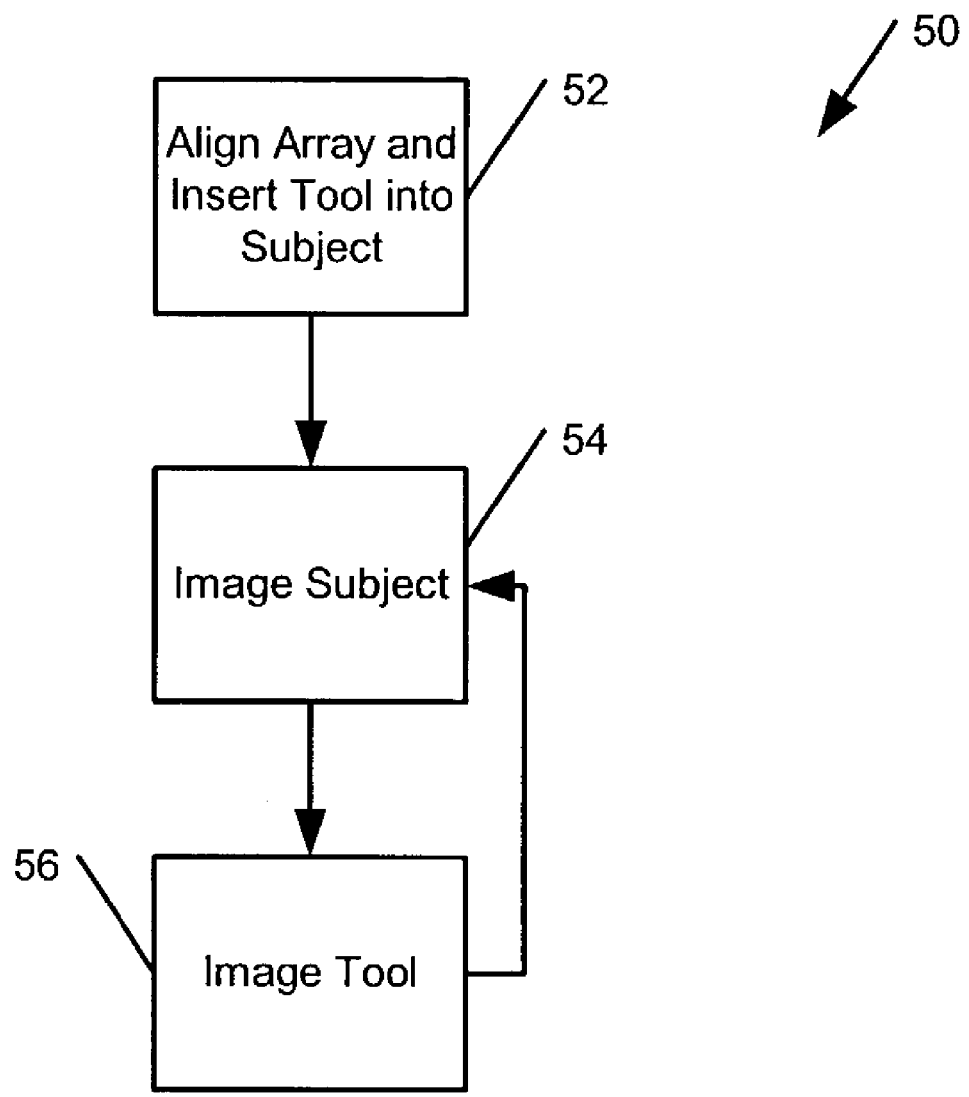
FIG. 5 is a block flow diagram of a process of using the system shown in FIG. 1.

In operation, referring to FIG. 5, with further reference to FIGS. 1–2, a process 50 for monitoring the position of the instrument tip 34 using the system 10 includes the stages shown. The process 50, however, is exemplary only and not limiting. The process 50 can be altered, e.g., by having stages added, removed, or rearranged.

At stage 52, the array 20 is aligned, the fiber 18 is attached to the instrument 12, (the fiber 18 may be pre-fabricated inside the instrument 12, to be a "part of" the instrument) and the instrument 12 is inserted into the subject 14. The array 20 is positioned to image a desired portion of the subject 14, i.e., where the tip 34 of the instrument 12 is to be inserted. The instrument 12 with the position indicator 18 attached is inserted into the subject 14 in the field of view of the array 20. The instrument 12 may be inserted in the vasculature of the subject 14 or through other tracks of the subject 14 that guide the instrument 12, although this is not required.

At stage 54, the imager 16 images the subject 14. During this time, the position indicator 18 is preferably not excited/transmitting. The processor 22 causes the array 20 to transmit ultrasound signals into the subject 14 and to receive reflected signals from the subject 14. The array 20 converts the reflected ultrasound signals to electrical signals and transfers these electrical signals to the processor 22. The processor 22 associates returned-signal amplitudes with pixels by determining the roundtrip time for the signals to emanate from and return to the array 20, in conjunction with the angles of the signals with respect to the array 20. The processor 22 converts these amplitudes into intensities associated with the pixels and transfers this information to the display 24 for display of a subject image corresponding to the imaged region of the subject 14.

Figure 6:
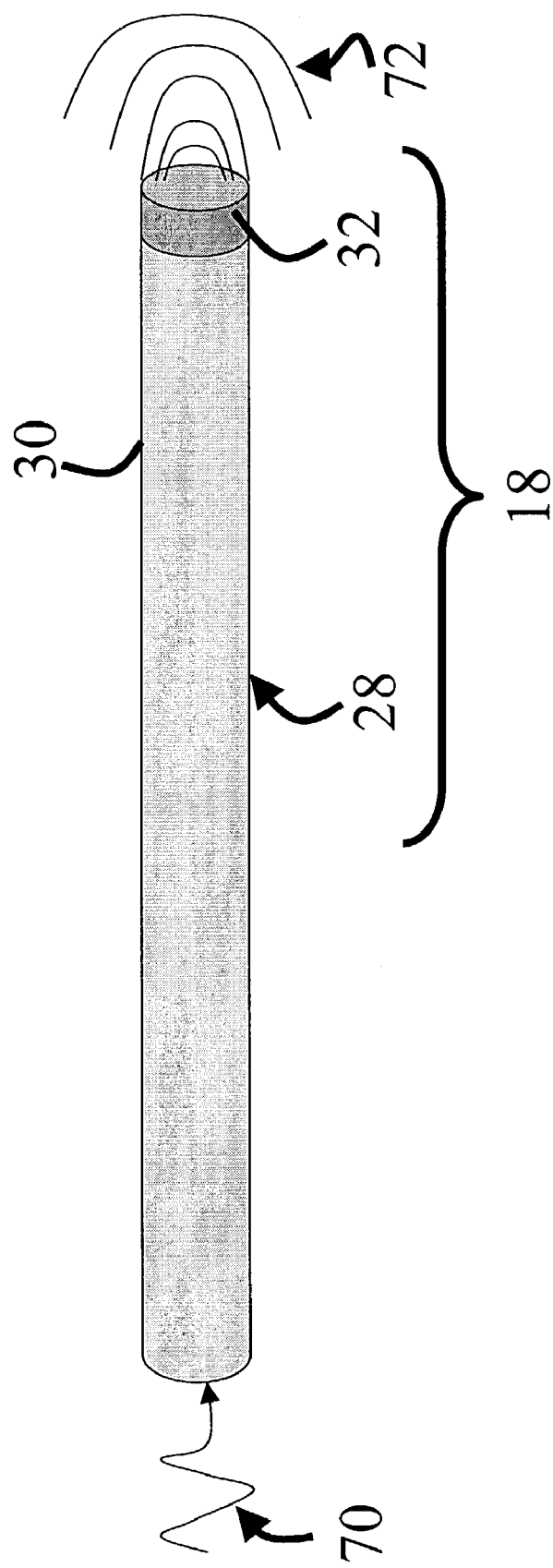
FIG. 6 is a perspective view of the position indicator shown in FIG. 2 in use.

At stage 56, the imager 16 images the position indicator 18. During this time the array 20 preferably does not transmit. Referring also to FIG. 6, the processor 22 causes the optical driver 26 to send light pulses 70 through the fiber 28 to the position indicator 18. The coating 32 of the indicator 18 absorbs the light and through the photoacoustic effect produces ultrasound waves 72 that radiate from the coating 32. These ultrasound waves travel through the subject 14 forming subject-influenced ultrasound signals, related to but different from the emitted waves, that are received by the array 20. The array 20 converts the indicator's ultrasound signals to electrical signals and transfers these electrical signals to the processor 22. The processor 22 associates signal amplitudes with pixels by determining the one-way travel time for the signals to emanate from the coating 32 and reach the array 20, in conjunction with the angles of the signals with respect to the array 20. The distance between the position indicator 18 and the array 20 is determined by measuring the time difference between the onset of the optical pulse at the proximal end of the fiber 28 and the time the signal is received by the array 20 multiplied by the speed of sound in the tissue. The time delay between the onset of the optical pulse and its absorption at the distal end is negligible, since the velocity of light in the fiber 28 is much faster than that of sound in the tissue. The processor 22 converts these amplitudes into intensities associated with the pixels and transfers this information to the display 24 for display of a position indicator image.

The stages 54 and 56 are alternated such that the display 24 provides a superposition of the subject image in the region of the indicator, and the position indicator image. The superimposed images thus show the indicator's position relative to the subject 14. The processor 22 controls the array 20 and the optical driver 26 to alternate which image is determined. The alternating cycles may not image the subject 14 and the indicator 18 with equal frequency.

Alternatively, at stage 56 the array 20 continues to transmit and receive ultrasonic waves. The position indicator 18 is programmed to transmit acoustic waves at alternating cycles, e.g., it is turned on in one imaging cycle (or a certain number of cycles), termed "ON cycles," and then turned off at the following imaging cycle/cycles, termed "OFF cycles," of the array 20. During consecutive ON-OFF imaging cycles, the probe of array 20 is preferably not moved relative to the subject 14. Both images are stored in the memory of the processor 22. Consequently, when the image obtained by the array 20 during the ON cycle is compared (e.g., by signal processing such as subtraction, high-pass filtering, etc.) to the image obtained during the OFF cycle, the indicator's position can be highlighted. Once the position indicator's signal is identified, its distance can be determined from measuring the time difference between the onset of the optical pulse in the fiber 28 and the time the signal is received by the array 20 multiplied by the speed of sound in the tissue. Such a configuration uses additional signal processing instruments to extract the position of the indicator 18, and may be used, e.g., in cases where the transmitter of the array 20 cannot be turned on and off periodically.

Figure 12:
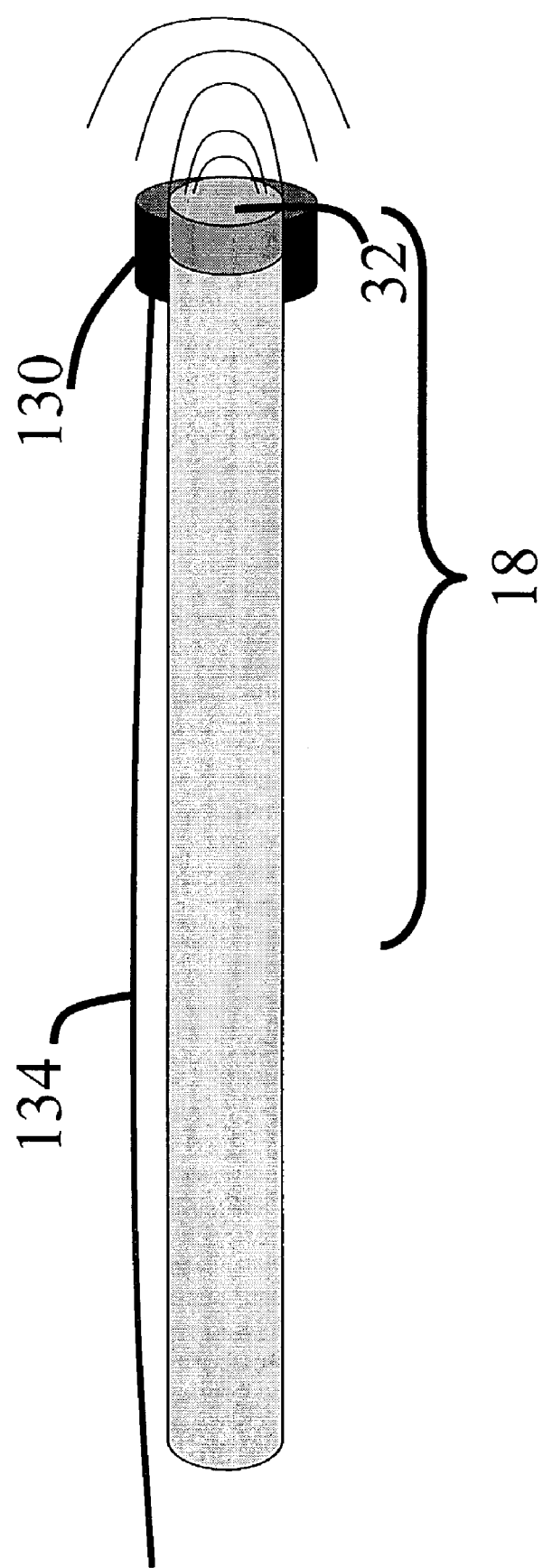
FIG. 12 is a simplified perspective view of a position indicator integrated with an acoustic sensor.

Alternatively still, referring to FIGS. 1 and 12, an acoustic sensor 130 is placed in the vicinity of the position indicator 18. This sensor 130 may be an ultrasound transducer (such as a thin PVDF film, connected to the processor 22 via electric wires 134) or an optical transducer. The ultrasound signals transmitted from the array 20 are detected by the sensor 130 and transmitted to the processor 22. In response to the detected incident ultrasound signals, the processor 22 provides excitation signals to produce acoustic signals from the indicator 18. In this case, due to the relative speeds of sound and light, the produced acoustic signal will essentially coincide with the reflected ultrasound signals for imaging.

Position indicators may be used that do not include a photoacoustic material. In such instances, light that propagates through the fiber 28 emanates from a distal end of the fiber 28 and irradiates portions of the subject 14 near the distal end of the fiber 28. For example, in a human subject, the emitted light can irradiate tissues or walls surrounding a cavity or vessel containing the instrument 12. As the emitted light is absorbed by the surrounding material, a photoacoustic effect occurs and an acoustic signal is generated in the tissue itself and travels to, and is received by, the array 20. Acoustic signals produced in tissue provide information about the optic and acoustic properties of the tissue. Different tissues have different optic and acoustic properties and thus different tissues may be discerned based upon the acoustic waves received by the array 20. Different tissues or different states of tissue (for example oxygenated or ischemic) absorb different wavelengths of light. Further, a photoacoustic signal is generated only when light is absorbed by the tissue. Therefore, by using different wavelengths of light and monitoring the photoacoustic signal, it can be determined which tissues are excited and their properties.

Further, photoacoustic materials may be disposed on instruments, preferably at the tip or other known location(s) on each instrument, such that light emitted from an uncoated fiber irradiates, and is absorbed by, the photoacoustic material on the instrument. This material produces acoustic signals in response to the absorbed light that can be received by the array 20 and further processed. In some embodiments, coating materials that absorb at different spectral bands may be used. In such embodiments, different wavelengths may be used to induce acoustic signals via the photoacoustic effect, while other wavelengths may pass through the coating and illuminate the tissue directly to perform ablation of plaques or myocardial tissue for example. Position indicators may be configured without optical fibers, or with other means of transmitting light.

Figure 7:
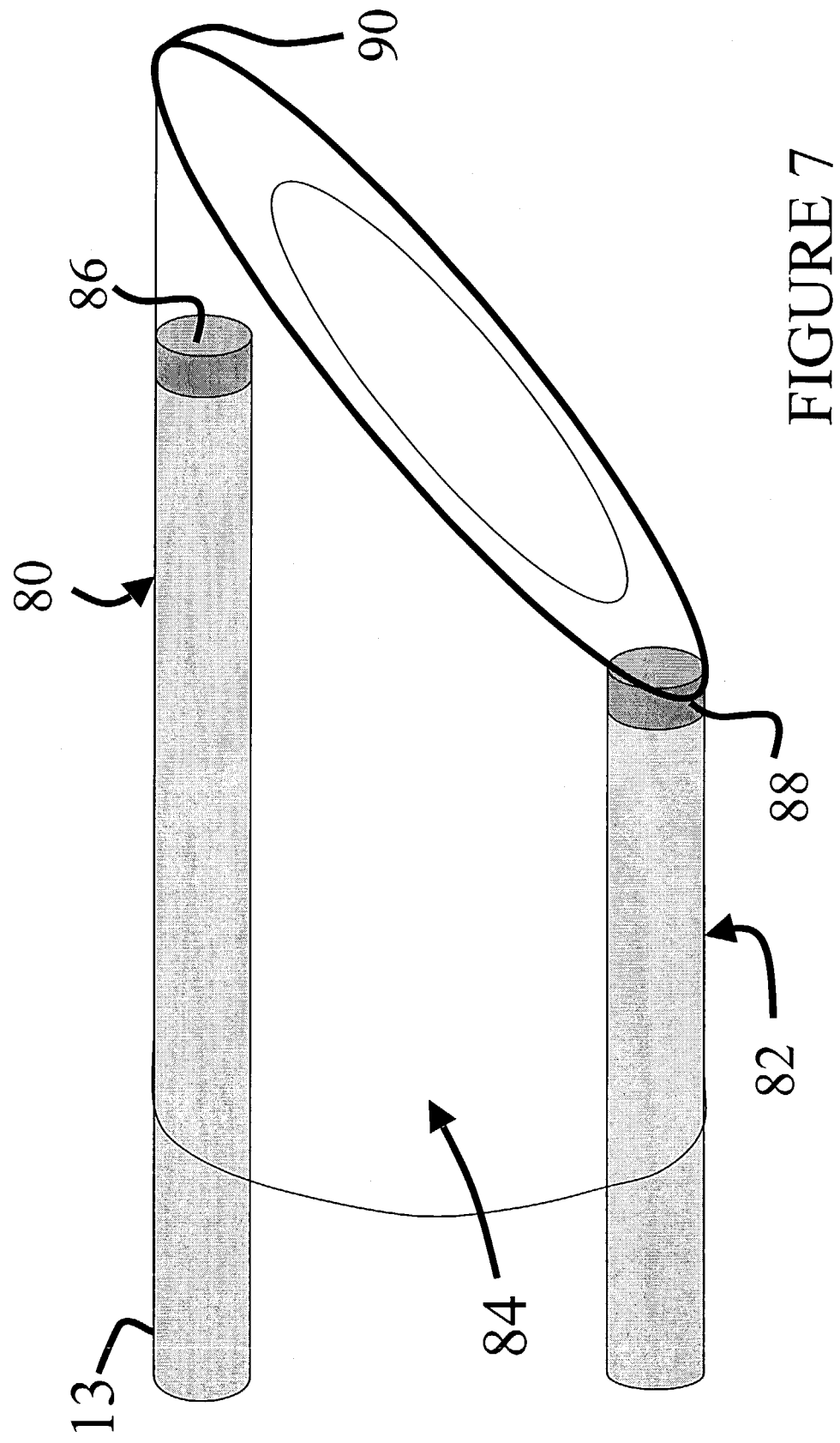
FIG. 7 is a simplified, see-through perspective view of two position indicators disposed in a needle.

Also, multiple position indicators may be used with a single instrument. Referring to FIG. 7, two position indicators 80, 82 are provided with an instrument 84. Coatings 86, 88 of the indicators 80, 82 are preferably disposed at known distances from a tip 90 of the instrument 84 and from each other. The coatings 86, 88 are configured to provide different frequencies of ultrasound such that they may be distinguished during processing and display. Alternatively, or additionally, the indicators 80, 82 may be excited at different times to provide for distinguishing the indicators 80, 82.

With multiple position indicators, operation to monitor their positions preferably includes determining the acoustic signature of the position indicators before insertion into the subject 14. For example, the tips of position indicators 80, 82 may be placed within the field of view of the array 20 and the optical driver 26 actuated to supply optical signals to the indicators 80, 82. The coatings of indicators 80, 82 absorb the signals and produce acoustic waves that the array 20 receives and converts to electrical impulses that are sent to the processor 22. The processor 22 discerns the different frequencies produced and associated the various frequencies with the corresponding indicators 80, 82. If the indicators 80, 82 are distinguished using different time triggering, the processor 22 associates the excitation times with the appropriate indicators 80, 82. The time difference between optical triggering of the different indicators 80, 82 should be larger than the maximum distance between the position indicators 80 and 82 divided by the speed of sound in the tissue, to avoid confusion between the indicators 80, 82.

During monitoring of multiple position indicators, e.g. the indicators 80, 82, the position, shape, and/or tip location, of the instrument 12 can be determined. With known locations of the tips of indicators 80, 82 relative to the tip 90, the location of the tip 90 can be extrapolated from the positions of the tips of indicators 80, 82 if the instrument 84 is rigid, at least in the vicinity of the tip 90 and the indicators 80, 82. Consequently, a "virtual" position indicator for the tip 90 may be added on the display. The position of the virtual indicator can be extrapolated from the known distance between the tip of indicator 80 and the tip 90 of the instrument 84, and from the orientation of the instrument calculated according to the positions of the tips of indicators 80 and 82 respectively. If the instrument 84 is flexible, the indicators 80, 82 can be used to determine the flex or bend of the instrument 84. To do this, preferably more than two indicators are used on the instrument 84. The locations of the tips of indicators 80, 82 will also indicate an orientation of the instrument 84. To provide a frame of reference for the orientation of the instrument 84, fiduciary markers (that may be other position indicators similar to the indicators 80, 82) may be placed at known locations inside and/or outside of the subject 14.

Such a configuration can serve to monitor the insertion of a needle or a knife under ultrasound guidance. Currently, a "needle guide" trajectory is calculated prior to the insertion of a needle or knife into the body. A virtual trajectory is drawn on the display unit used by the operator. The operator tries to direct the tip of a needle or knife along the direction of the virtual line. If the needle bends or flexes, however, the operator might be guiding a different part of the instrument, misjudging it to be the tip. The invention can be used to monitor the position of the tip of the instrument relative to the calculated virtual "needle guide," and serve to warn the operator by a beep or other type of alarm that the instrument is misplaced relative to the needle guide trajectory. In addition, by measuring the flexure or orientation of the instrument, the system can calculate (or extrapolate) the future trajectory of the instrument and warn the operator prior to a displacement relative to the needle guide trajectory. Such a warning system is particularly important when performing minimally invasive procedures in the brain or thyroid gland, which require thin needles that can bend easily, and high-precision instrument manipulation is needed in order to prevent serious injury.

Figure 8:
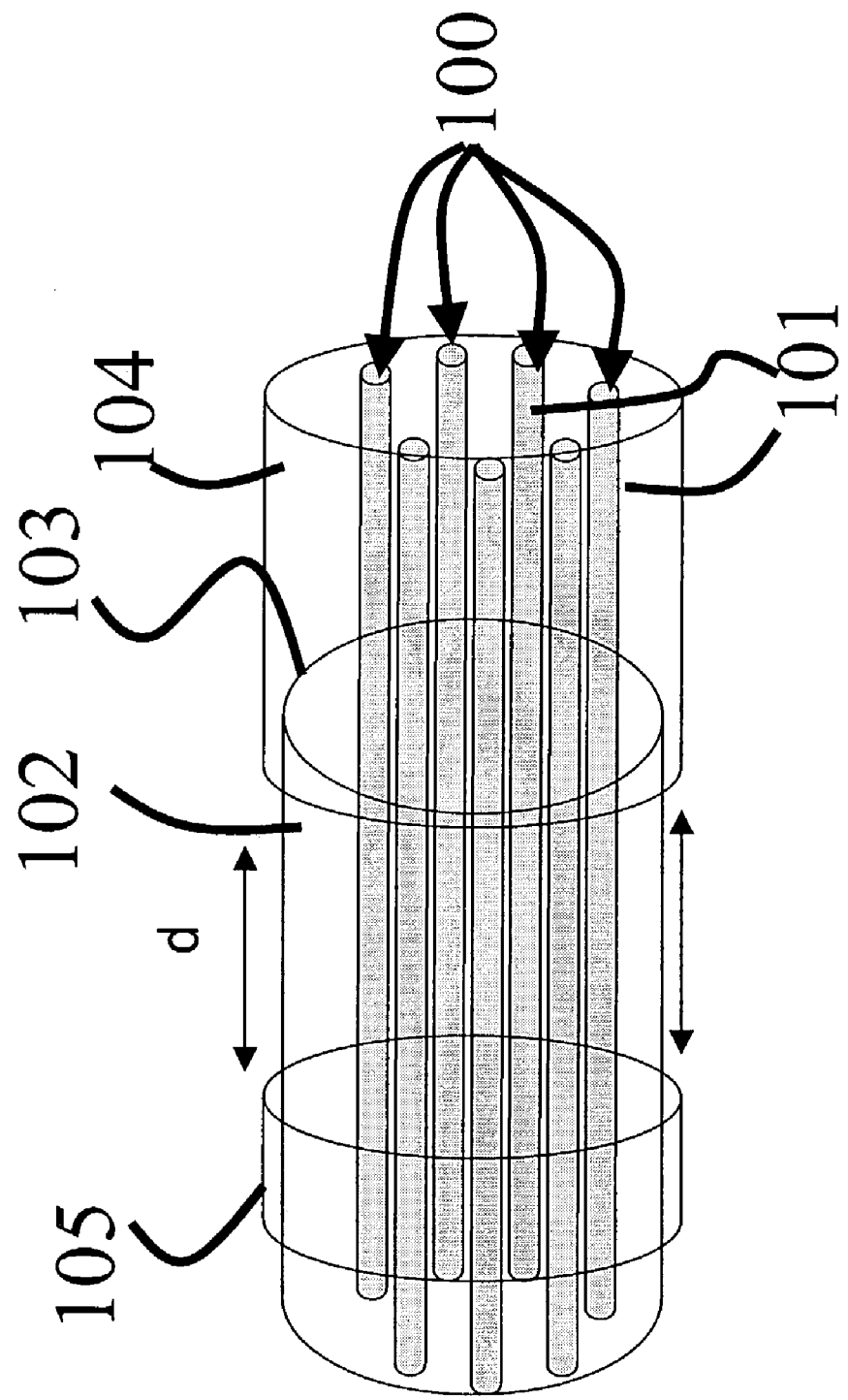
FIGS. 8–9 are simplified, see-through perspective views of multiple position indicators disposed in a catheter with a retractable sleeve, with the sleeve in a closed position and a retracted position, respectively.
Figure 9:
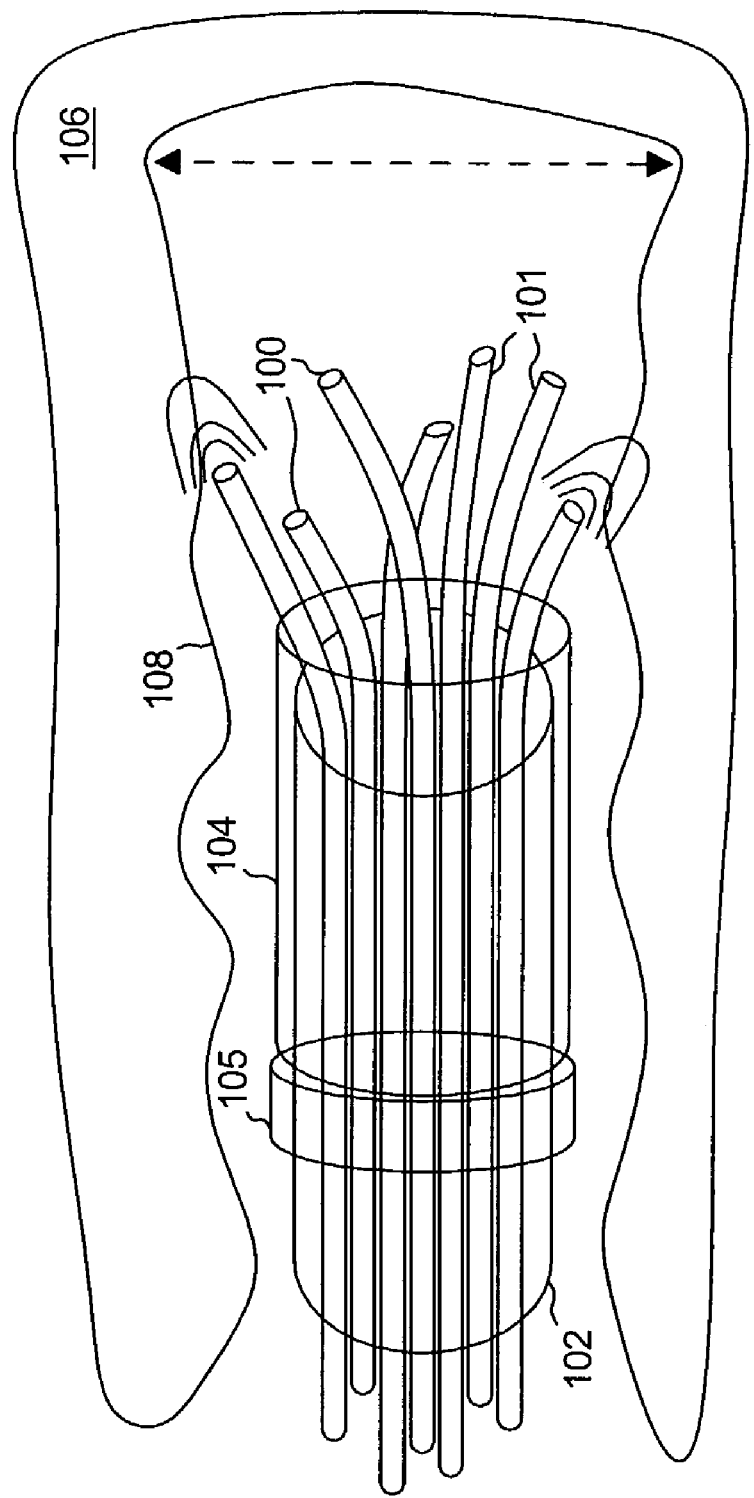

Referring to FIG. 8, many position indicators 100 can be placed in an instrument such as a catheter 102 as shown, e.g., for mapping vessels of a subject. Fibers 101 of the indicators 100 are very flexible and have a diameter of several tens of microns. The catheter 102 is configured (e.g., micromachined) to contain tracks (e.g., cylindrical tracks) to hold the position indicators 100 in the catheter 102. The indicators 100 may be held in the catheter 102 such that their tips are disposed in a desired orientation at the tip 103 of the catheter 102. Referring also to FIG. 9, a sleeve 104 encapsulates, but does not fixedly hold in place, the position indicators 100 outboard of the catheter's tip 103. The sleeve 104 encapsulates the indicators 100 during insertion of the catheter 102 into the subject 106. When a desired position in a vessel 108 of the subject 106 (e.g., part of the subject's vasculature) is reached, the sleeve 104 is retracted along a length of the catheter to a retracted position shown in FIG. 9 at which point the sleeve 104 is stopped by a stopper 105. In the retracted position, the position indicators 100 are able to flex outwardly until they reach a wall of the vessel 08 or fully extend. Preferably, the indicators 100 are configured such that they will span the breadth of the vessel 108. The catheter 102 can be moved, e.g., pulled proximally, along the vessel 108 and the locations of the position indicators 100 monitored to yield a mapping of the geometry of the vessel 108. Preferably approximately 10 to 5000 position indicators 100 are used depending upon the geometry of the vessel 108 (e.g., diameter of about 1–8 mm), the diameters of the fibers 101 (e.g., 50–600 μm) and the desired resolution for mapping the vessel 108 (e.g., possibly very few, such as 10, indicators 100 would suffice). A three-dimensional image of the vessel 108 can be determined by moving the catheter 102 in the vessel 108 at a constant speed and obtaining images at constant time intervals.

Figure 10:
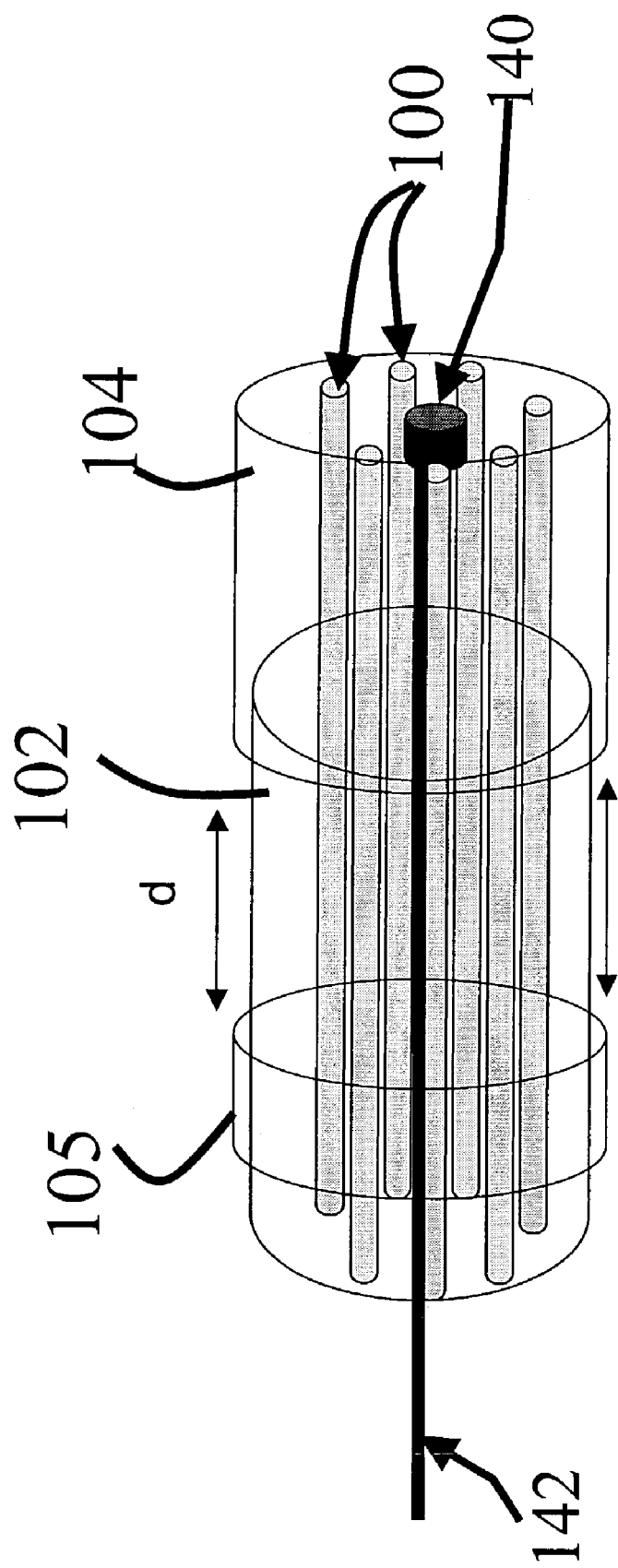
FIG. 10 is a simplified, see-through perspective view of multiple position indicators disposed in a catheter with a retractable sleeve, with the sleeve in a closed position, and with a sensor disposed among the indicators.

Referring to FIG. 10, a sensor 140 can be placed among the indicators 100. The sensor 140 is an acoustic transducer that can be connected to the processor 22 (FIG. 1) via a line 142 (e.g., a wire, or an optical fiber if the sensor 140 is an optical transducer). Signals produced by the sensor 140 are conveyed to the processor 22 for analysis. If the various indicators 100 are excited individually, then the processor 22 can determine the respective distances from the sensor 140 to the tips of the indicators 100 using the difference between the excitation times of the indicators and the reception times at the sensor 140 of the sounds produced by the indicators 100, and the speed of sound in the subject (e.g., in blood). Thus, this additional information regarding the distances of the indicator tips to the sensor 140 (e.g., in the middle of the instrument 102) can be used in mapping the vessel in which the instrument 102 is disposed. The resolution provided by the sensor 140 will depend on the geometry of the indicators 100, e.g., several tens of microns. If the sensor 140 is an ultrasound imager, the indicators 100 can serve as acoustic sources for acoustic energy. The energy reflected or scattered from internal structures is detected by the imager 140. Such a configuration provides multidirectional imaging of internal structures and reduces (if not eliminates) the need to supply high voltage to a conventional ultrasound transducer for emitting ultrasound radiation intravascularly.

The system described above may be used to monitor the insertion of a balloon catheter or a stent into the vascular system. As the insert expands (the balloon is inflated), its size can be monitored directly by the system shown in FIGS. 8–10. A warning indicator may alert the operator prior to possible rupture of the blood vessel by the expanding insert.

Figure 11:
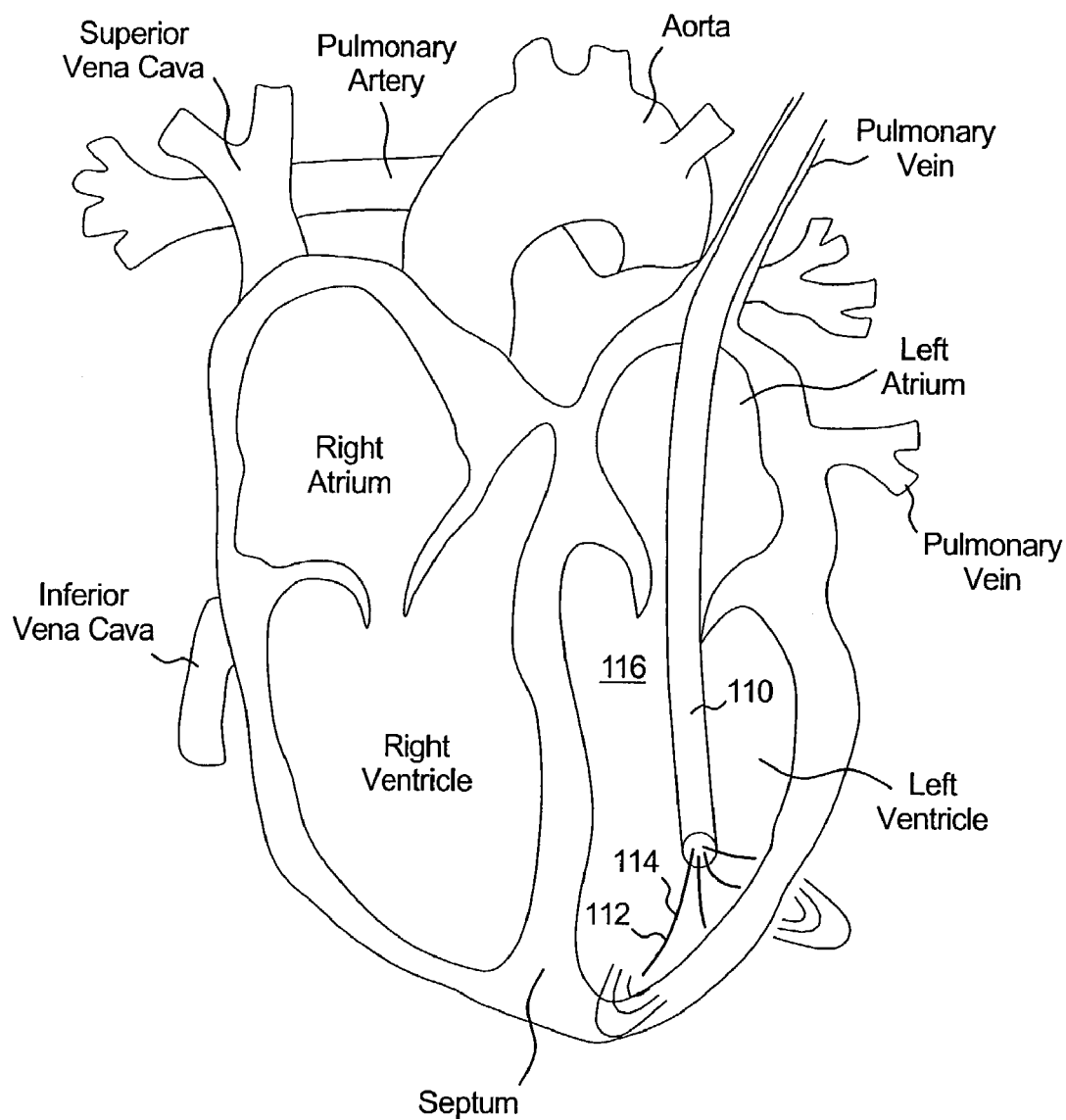
FIG. 11 is a simplified, cut-away view of a human heart and multiple position indicators disposed in a catheter in a deployed state.

Cavities can also be mapped using an instrument and indicators similar to those shown in FIGS. 8–9, with some adjustments. Referring to FIG. 11, a catheter instrument 110 includes fiber position indicators 112. The catheter is configured, e.g., micromachined, to contain a preferably small number, here four, of indicators 112. The lengths of fibers 114 of the indicators 112 that are not fixedly contained by the catheter 110 is preferably greater than those of the configuration shown in FIGS. 8–9 for mapping vessels. Likewise, the angles that the fibers 114 can form with respect to the instrument 110 are preferably greater than those for the vessel-mapping configuration. The instrument 110 is inserted into a cavity 116 of a subject 118 (here, a chamber of a human heart) until the instrument 110 contacts a wall of the cavity 116, and the indicators 112 are deployed. The indicators 112 can be deployed according to various mechanisms, e.g., by being triggered by an external system or by internal events (such as temperature change or biochemical reactions), etc. The indicators 112 are allowed to reach walls of the cavity 116, and the instrument 110 is moved while images are taken of the position indicators 112 contacting the cavity walls. The positions of the indicators 112 are determined, and can be mapped according to the ultrasound image of the subject 118. From the relative positions of indicators 112, the volume of the cavity 116 can be calculated. For example, the direct measurement of cardiac output could be determined using this technique.

Still other embodiments are within the scope and spirit of the appended claims. For example, due to the nature of software, functions implemented by the processor, or other devices, as described above can be implemented using software, hardware, firmware, hardwiring, or combinations of any of these. Features implementing functions may also be physically located at various positions, including being distributed such that portions of functions are implemented at different physical locations. Further, the array 20 may take various forms, including multiple transducers that are displaced from each other, e.g., to determine positions of the indicator 18 using triangulation.

What is claimed is:

1. A system for monitoring a position of an instrument in a subject comprising:

a light transmission medium configured to transmit light pulses to a desired region to produce an acoustic signal, wherein the light transmission medium is an optical fiber;

at least one ultrasound sensor configured to receive the acoustic signal and to produce a transduced signal from the acoustic signal;

a processing unit connected to the at least one ultrasound sensor and configured to locate a source of the acoustic signal using the transduced signal; and a photoacoustic transducer including a photoacoustic material disposed in the desired region to absorb light transmitted by the light transmission medium to produce the acoustic signal, wherein the photoacoustic material is disposed at an end of the optical fiber, and wherein the photoacoustic material is a first photoacoustic material configured to produce a first frequency of sound from absorbed light, the system further comprising a second photoacoustic material configured to produce a second frequency of sound from absorbed light and coupled to the fiber distally from the first material, the first photoacoustic material being disposed and configured to absorb a first portion of light transmitted by the light transmission medium and to pass a second portion of the light transmitted by the light transmission medium.

2. The system of claim 1 wherein the optical fiber is coupled to the instrument.

3. The system of claim 2 wherein the end of the optical fiber, on which the photoacoustic material is disposed, is disposed a known distance from an end of the instrument.

4. A system for monitoring a position of an instrument in a subject comprising:

a light transmission medium configured to transmit light pulses to a desired region to produce an acoustic signal, wherein the light transmission medium comprises a plurality of optical fibers and the system further comprises position indicators coupled to the plurality of fibers;

at least one ultrasound sensor configured to receive the acoustic signal and to produce a transduced signal from the acoustic signal;

a processing unit connected to the at least one ultrasound sensor and configured to locate a source of the acoustic signal using the transduced signal; and a photoacoustic transducer including a photoacoustic material disposed in the desired region to absorb light transmitted by the light transmission medium to produce the acoustic signal, wherein the photoacoustic material is disposed at an ends of the optical fibers.

5. The system of claim 4 wherein the position indicators comprise photoacoustic transducers including different photoacoustic materials configured to produce different frequencies of ultrasound signals, and wherein the processor is configured to distinguish between the photoacoustic transducers in accordance with the respective frequencies associated with the photoacoustic materials.

6. The system of claim 4 further comprising an optical driver coupled to the processor, wherein the processor is configured to cause the optical driver to provide optical signals to the plurality of optical fibers at different times, and wherein the processor is configured to distinguish between the position indicators in accordance with respective excitation times of the position indicators.

7. The system of claim 4 further comprising the instrument, wherein the position indicators are coupled to the instrument and have ultrasound-emitting portions that are disposed at least one of at known locations relative to the instrument and at known locations relative to each other.

8. The system of claim 4 further comprising a sensor disposed among the plurality of position indicators and coupled to the processor, the processor being further configured to determine distances from the sensor to the position indicators in response to information provided to the processor by the sensor.

9. The system of claim 4 further comprising the instrument, the instrument being further configured to selectively contain the plurality of position indicators and deploy ultrasound-emitting portions of the position indicators outside of the instrument.

10. The system of claim 9 wherein the instrument comprises a retractable sleeve for selectively containing and deploying the position indicators.

11. A system for monitoring a position of an instrument in a subject, the instrument being configured to be inserted into the subject, the system comprising:

an array of ultrasound transducers configured to translate between ultrasound signals and electrical signals;

an optical driver configured to provide optical excitation signals;

a position indicator including an optical fiber, coupled to the optical driver and attached to the instrument, and a photoacoustic material disposed to absorb light transmitted by the optical fiber;

a display configured to provide images in response to control signals; and a processor connected to the transducers, the optical driver, and the display, and configured to;

actuate the array to emit ultrasound signals into the subject;

receive first electrical signals from the array indicative of reflections of the emitted ultrasound signals;

process the first electrical signals into first control signals indicative of a first image of the subject and to convey the first control signals to the display;

actuate the driver to provide an excitation signal to the optical fiber;

receive a second electrical signal from the array indicative of an ultrasound signal produced by the photoacoustic material;

determine a position of the instrument from the second electrical signal; and process the second electrical signal into a second control signal indicative of a second image of the instrument and to convey the second control signal to the display.

12. The system of claim 11 wherein the processor is configured to control the display to provide the images from the first and second control signals such that the first and second images at least appear to be provided concurrently.

13. The system of claim 11 wherein the processor is configured to actuate the transmission from the array and to actuate the optical driver at different, alternating times.

14. An instrument for use with an ultrasound imager for monitoring positions associated with the instrument while the instrument is disposed in a subject, the instrument comprising:

a body having a proximal end and a distal end, the body being configured to be inserted into the subject;

a first optical fiber coupled to the body and having a distal end disposed adjacent to the distal end of the body; and a first photoacoustic material on the first optical fiber configured to transduce optical signals received from the first optical fiber into first ultrasound signals and to emit the first ultrasound signals into the subject, wherein the distal end of the first optical fiber is disposed a known distance from the distal end of the body.

15. The instrument of claim 14 further comprising:

a second optical fiber coupled to the body and having a distal end; and a second photoacoustic material on the second optical fiber, the second photoacoustic material configured to transduce optical signals received from the second optical fiber into second ultrasound signals and to emit the second ultrasound signals into the subject, the first and second photoacoustic materials being configured such that frequencies of the first and second ultrasound signals are different.

16. The instrument of claim 15 wherein the first and second optical fibers are fixedly coupled to the body along portions of their lengths and distal portions of their lengths releasably contained by the body.

17. The instrument of claim 16 wherein the body includes a sleeve for releasably containing the distal portions of the optical fibers, the sleeve being movable between a first position for containing the distal portions of the fibers and a second position for deploying the distal portions of the fibers.

18. The instrument of claim 15 further comprising an acoustic sensor, configured to transduce acoustic signals, coupled to the body.

19. The instrument of claim 14 wherein the body is configured to be inserted into a human.

20. A system for monitoring the position of an instrument in a subject, the instrument being configured to be inserted into the subject, the system comprising:

a plurality of ultrasound transducers configured to translate between ultrasound signals and electrical signals;

driver means coupled to the ultrasound transducers for providing first excitation signals to the ultrasound transducers and for providing second excitation signals;

position indicator means coupled to the driver and to the instrument for producing ultrasound signals in response to the second excitation signals from the driver means; and processor means, coupled to the transducers and the driver means, for controlling the driver means to cause the transducers to transmit first ultrasound signals into the subject, for determining an image of the subject from reflected subject signals related to the first ultrasound signals, for controlling the driver means to cause the position indicator means to produce a second ultrasound signals, for determining an indicator image corresponding to the position indicator means from indicator signals related to the second ultrasound signal, and for controlling a display to show an association between the indicator image and the image of the subject.

21. The system of claim 20 wherein the driver means includes an electrical driver coupled to the transducers and an optical driver coupled to the position indicator means.

22. The system of claim 20 wherein the position indicator means includes a photoacoustic material on an optical fiber.

23. The system of claim 22 wherein the position indicator means includes multiple optical fibers each having a photoacoustic material on a respective tip.

24. The system of claim 23 wherein different optical fibers of the position indicator means have different photoacoustic material characteristics that produce different frequencies of ultrasound.

25. The system of claim 20 wherein the position indicator means comprises multiple ultrasound emitters, the system further comprising an acoustic sensor configured to receive and transduce ultrasound from the multiple ultrasound emitters, and to transmit the transduced information to the processing means that is further for determining distances from the acoustic sensor to the multiple ultrasound emitters.

* * * * *